United States Patent [19]
Perdreaux, Jr.

[11] 3,956,826
[45] May 18, 1976

[54] ULTRASONIC DEVICE AND METHOD

[75] Inventor: Rene J. Perdreaux, Jr., New York, N.Y.

[73] Assignee: Cavitron Corporation, New York, N.Y.

[22] Filed: Mar. 19, 1974

[21] Appl. No.: 452,627

[52] U.S. Cl............................. 32/58; 32/DIG. 4; 128/24 A; 128/62 A; 128/66
[51] Int. Cl.² ........................................... A61C 3/06
[58] Field of Search ............. 32/58, DIG. 4, 46, 50; 128/24 A, 303 R, 303.1, 62 A, 66

[56] References Cited
UNITED STATES PATENTS

| | | | |
|---|---|---|---|
| 3,058,218 | 10/1962 | Kleesattel et al. | 128/24 A |
| 3,213,537 | 10/1965 | Balamuth et al. | 128/24 A |
| 3,375,583 | 4/1968 | Blank et al. | 128/24 A X |
| 3,522,801 | 8/1970 | Robinson | 128/62 A |
| 3,589,363 | 6/1971 | Banko | 128/24 A |
| 3,645,255 | 2/1970 | Robinson | 128/24 A |
| 3,809,977 | 5/1974 | Balamuth et al. | 128/24 A |

*Primary Examiner*—Louis G. Mancene
*Assistant Examiner*—Jack Q. Lever

*Attorney, Agent, or Firm*—Philip H. Pohl; Philip Sperber

[57] ABSTRACT

An ultrasonic hand-held cleaning device having a housing enclosing a casing, an energyzing winding about the casing, and a fluid conduit attached to the interior of the casing. A sleeve is insertably mounted into the end of the casing, and acts to support a connecting body at a spaced distance within the sleeve so as to form an annular space in fluid communication with the casing. A vibrator is attached at the casing end to the connecting body and is therefore located in the casing opposite the energyzing winding. A cleaning tool is attached at the other end of the connecting body. In one version fluid moving through the annular space is sprayed out an annular nozzle around the tool which is itself vibrating ultrasonically as a result of reverbretory vibrations induced by the vibrator. In a second preferred embodiment the connecting body has a ring at its nodal point, the sleeve being cut out to accomodate the ring and having two longitudinal slots for the passage of fluid. A tubular insert for controlling the space between the connecting body and the sleeve at the nozzle is supported by the sleeve.

15 Claims, 5 Drawing Figures

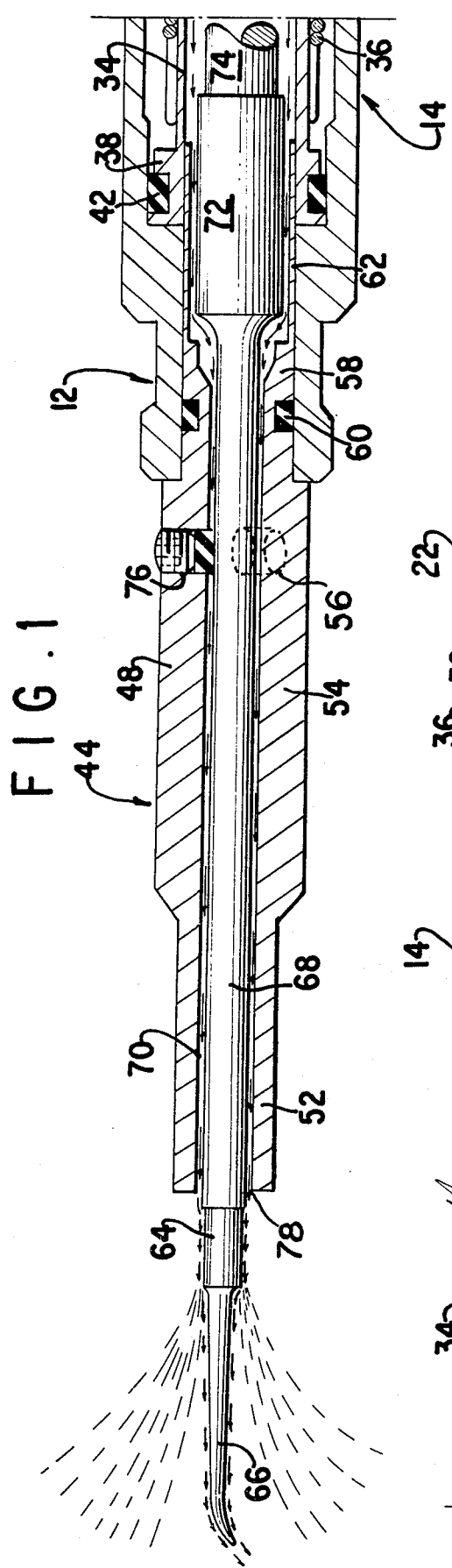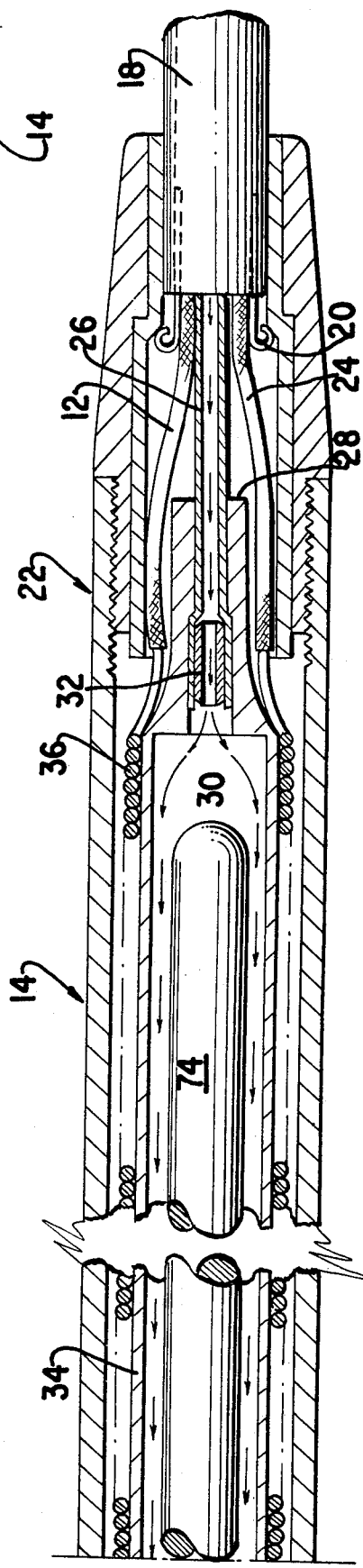

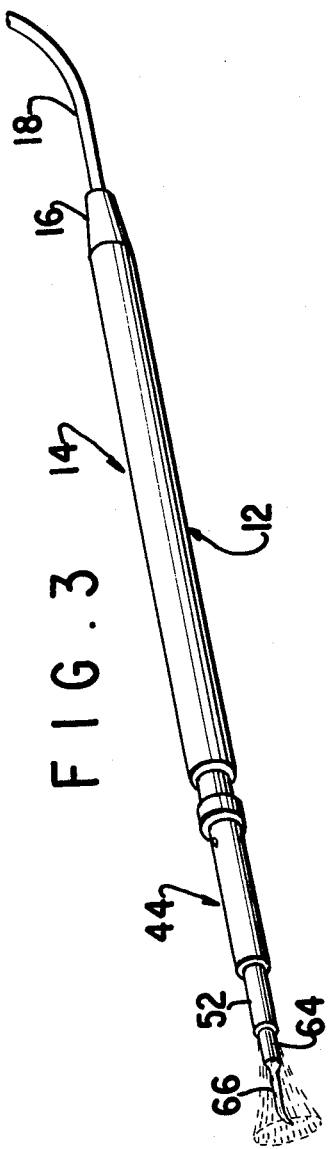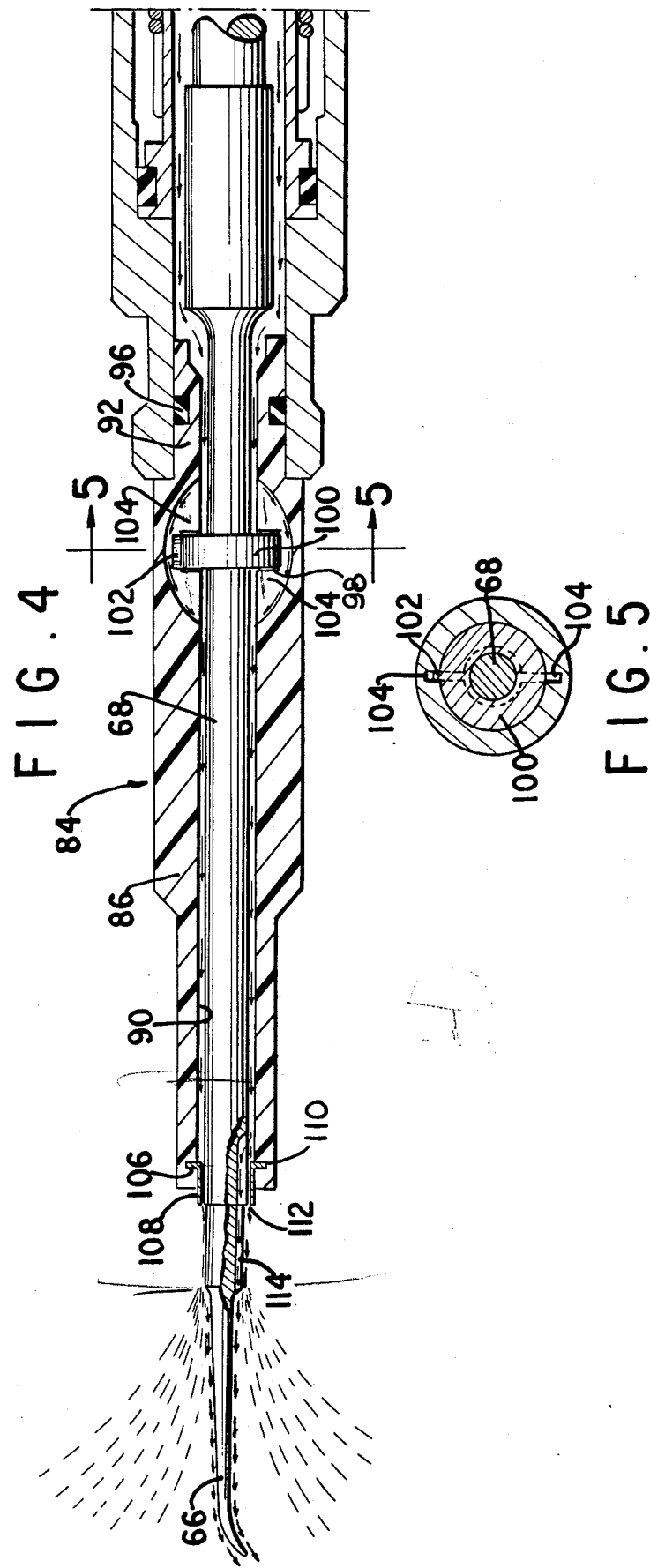

3,956,826

ULTRASONIC DEVICE AND METHOD

BACKGROUND OF THE INVENTION

This invention relates to an improved ultrasonic dental tool. More particularly this invention relates to apparatus which utilizes an ultrasonically driven head in conjunction with a spray of liquid or slurry containing abrasive material to operate as a cutting or cleaning tool in dental operations (procedures).

Acoustically vibrated cutting and cleaning devices essentially comprise a vibrator having an electromechanical part or section which is induced to vibrate at relatively high frequency and small amplitude by the presence of a surrounding alternating electromagnetic field as produced by an alternating current source. The electromechanical section or part may be any one of several types such as electrodynamic, piezo-electric, or magnetostrictive, with an operating frequency range in the order of 5,000 to 40,000 cycles per second and a preferred frequency range in the order of 20,000 to about 30,000 cycles per second.

Where the electromechanical section or part is magnetostrictive, one end thereof is fixed to a connecting body whose other end rigidly supports a selected work tool. The connecting body serves as an acoustic impedance transformer and is so shaped and formed as to either enlarge or reduce the amplitude of vibrations produced by the electromechanical part or section as delivered to the work tool through the connecting body. The vibrator described above is essentially composed of an electromechanical part or section, a connecting body and a work tool, which are rigidly joined end to end as a unit and supported by a suitable housing or casing.

Specifically the present invention is an improvement on the device shown in U.S. Pat. No. 3,076,904 issued Feb. 5, 1963 to C. Kleesattel et al for Acoustically Vibrated Material Cutting and Removing Devices. Prior art devices as exemplified by the device shown in the heretofore described patent utilize a separate off-center conduit and nozzle to deliver a liquid slurry or cooling water to the tool and adjacent area. While there are no great disadvantages to such an offset conduit, the position of the tool and the nozzle must be set so that the liquid is delivered in the work area. For instance the nozzle may be so constructed to deliver water in the area of the tool tip for a tool which is bent away from the axis of the device. Obviously if an unbent tool tip were in use, the fluid will not be directed towards the more appropriate location unless the nozzle direction were changed. Secondarily where the nozzle tip stands out from the body of the device, it is more exposed to dislocation and damage.

SUMMARY OF THE INVENTION

Accordingly I have invented an improvement in an ultrasonic cleaning device having a tubular casing, an energizing winding around the casing, means for introducing fluid into one end of the casing the improvement which comprises a hollow sleeve having a portion insertable into the casing and in fluid communication therewith a tool assembly having a tip; a connecting body insertably mounted within the hollow sleeve; the connecting body having a diameter smaller than the hollow sleeve thereby providing an annular space between the connecting body and the hollow sleeve; and a vibrator which is actuated at an ultrasonic level, whereby fluid entering the casing passes through the casing through the annular space and out through the nozzle formed between the connecting body and the nozzle portion.

Preferably, means which are mounted between the sleeve and the connecting are in intermittent contact connecting body at the nodal point thereof.

A second preferred embodiment is described herein wherein the connecting body comprises a shank, with a ring transversely mounted on the shank at the nodal point thereof. The hollow sleeve has a transverse slot to accomodate the ring, and a flow detour means for conducting fluid around the ring. Preferably a bushing is mounted on the open end of the sleeve.

An object of my invention is to provide an improved ultrasonic cleaning device.

Another advantage is to provide an ultrasonic cleaning device having a novel and improved liquid nozzle.

Yet another object of the device according to the present invention is to provide an ultrasonic hand held device with a novel cooling means.

Another object of the device according to this invention is to provide a hand held ultrasonic device with reduced apparent vibration to the operator's hand.

Still another advantage of my invention is to provide an ultrasonic cleaning device having a novel liquid spray pattern.

Other objects and advantages of the present invention will be apparent to those skilled in the art from the description of the drawings and preferred embodiments which follow.

BRIEF DESCRIPTION OF THE DRAWINGS

FIG. 1 is a cross-sectional view of the forward end of the ultrasonic device according to my invention;

FIG. 2 is a view of the rear part of the device according to my invention;

FIG. 3 is a perspective view of the device;

FIG. 4 is a cross-sectional view of the forward part of another embodiment of the device according to the invention; and FIG. 5 is a sectional view taken along section 5-5 of FIG. 4.

DESCRIPTION OF THE PREFERRED EMBODIMENT

Acoustically vibrated cleaning devices are well known in the art. They assume many different forms and variations depending upon the design limitations, preferances, costs, materials, etc., as well as composition of the work piece and the work to be performed. The aforementioned U.S. Pat. No. 3,076,904 is illustrative of such devices as well as the various uses, permutations and modifications which may be utilized. Other permutations of such devices are illustrated by U.S. Pat. No. 3,368,280 issued Feb. 13, 1968 to G. M. Friedman et al for a Dental Tool and U.S. Pat. No. 3,075,288 issued Jan. 29, 1963 to L. Balamuth et al, for a Dental Instrument. My invention is an improved ultrasonic cleaning device for dental use which, among other things, advantageously introduces the liquid coolant to the work area. With this in mind, a preferred embodiment of my invention is shown in FIGS. 1-3 of the drawings in which the device 12 is shown in a cutaway elevational view with an outer tubular housing 14 suitable for holding in the palm of one hand much as a pencil is held. At the non-working end of the device, an endcap 16 is threaded to the housing through the end of which a flexible tubular conduit 18 extends into the body of the device 12. The conduit which is retained in the endcap in a relatively conventional manner as by clips 20 contains two conducting wires 22 and 24 and a fluid supply pipe 26, all three being from conventional sources not shown.

The fluid pipe 26 is inserted into the base 28 of a nipple section 30 and secured within the base by a pipe retainer 32. The nipple forms one end of a tubular casing 34 which extends axially within the housing. As shown each of the wires 22 and 24 are attached to each end of a helically coiled winding 36 of current conducting wire such as copper wire protected by a suitable coating e.g. enamel. The current in the winding induces an alternating electromagnetic field within the casing 34 when a current is passed therethrough. The casing may be formed of any suitable material such as a plastic or metal material which does not impede the establishment of the alternating electromagnetic field within the casing as produced by the winding. The casing is open at its anterior end, that end having an annular flange 38 with an annular groove. An elastomeric sealing element such as provided by O-ring 42 is secured within the groove and provides a tight fit and seal between the casing and the interior of the housing. Anterior to the flanged portion 38 of the casing the interior of the housing is reduced in diameter to substantially the same diameter as the interior of the casing. The housing wall abutting the anterior of the casing is counterbored and then beveled toward the casing anterior face. The front end of the housing has a smaller outside diameter but retains substantially the same interior diameter as the casing.

An insert assembly 44 is insertably mounted in the housing through the front end thereof. This is an important feature of this device in that the provision of the insert assembly 44 permits ready separation and removal of the insert assembly from the housing and replacement with another insert assembly having a different operating configuration. The outer part of the insert assembly 44 is a unitary sleeve 48 with a relatively small bore therethrough. The exterior diameter of the sleeve 48 varies between its different sections. That section closest to the tool end, the anterior section 52 is of a smaller outside diameter to reduce the weight of the device at this point but otherwise is as rigid as the other parts of the sleeve 48. A central section 54 of the sleeve is of greater outside diameter providing thereby sufficient material for three threaded holes 56 which are drilled and tapped transversely 120° apart through the sleeve center section. A third posterior section 58 of the sleeve has an outside diameter enabling it to be removably inserted into the anterior face of the housing in such surface to surface contact as to provide a tight fit therebetween. An annular slot is cut on the outside surface of the third section in which O-ring 60 is placed as a sealing and securing element. A fourth section 62 of the sleeve extends rearwardly from the third section and is essentially a thin walled tube with the same external diameter as the third section. The internal posterior face of the third section is countersunk to an extent which provides ease of fluid flow as described hereinafter.

A tool assembly 64 is slidingly held within the bores of the sleeve assembly though substantial parts of this assembly do extend out of each end of the sleeve. The tool assembly 64 comprises a tip 66 which is located out from the forward first section of the sleeve; the tip being generally a pointed relatively hard protrusion, though for various uses a 'soft' tip of rubber or plastic may be employed. The tip is permanently attached to one end of a solid tubular shank 68 of uniform diameter. The diameter of the shank is somewhat smaller than the interior bore diameter of the sleeve 48, so that there is an annular space 70 formed therebetween. The shank is long enough to extend through the sleeve bore to the area of the sleeve tube where the shank is machined to a larger diameter and thereby forms a connecting body 72. The connecting body 72 has a smaller diameter than the internal diameter of the sleeve and is therefore spaced apart from the interior of the sleeve tube extension. Brazed to the connecting body is a magnetostrictive vibrator 74 preferably formed of a metal alloy such as permanickel, nickel, permendeur or other alloys which possess high tensile strength, and is highly magnetostrictive in character. As seen in the drawing the vibrator 74 is longitudinally located within the interior of the casing and therefore is directly and intentionally electrodynamically subject to the imposed alternating currents passing through the winding. Thus the transducer is preferably vibrated in the frequency range of 10,000 to 40,000 cycles per second. This ultrasonic vibration is transferred through the connecting body and the shank to the tip which is thereby caused to vibrate in this range though with low amplitude. A longitudinal nodal point for the tool assembly is preferably located adjacent the central section of the sleeve at the point where the three threaded holes are located. Set screws 76 are threadedly secured in these holes, each screw tip being in contact with the connecting body. The set screws 76 preferably have 'soft' tips so as not to scour the hard surface of the connecting body.

In operation a high frequency alternating current is applied from an outside source (not shown) to the winding thereby inducing a high frequency vibration in the tool assembly and at the tip thereof. At the same time, a fluid, generally water is introduced via the conduit, passes through the pipe and into the casing, at which point there are relatively less cross section restrictions to the fluid flow. As the water leaves the casing it first enters the restrictive annular spaces between the connecting body and the sleeve extension and then the smaller annular space between the shank and sleeve finally emerging through a nozzle 78 formed by the shank and the end of the sleeve. Such an arrangement additionally functions to lubricate the shank and connecting body in the manner of a hydrostatic bearing while at the same time causing a fluid spray pattern as shown in FIG. 3 of the drawings, this pattern impinging around the operating tip of the device.

Similarly by functioning as a hydrostatic bearing utilizing the fluid flow pressure as lubricant the housing is substantially isolated from the ultrasonic vibration elements of the device. This is important for a device which is intended to be used as a hand held instrument, since the operator's hands may possibly be sensitive to any kind of vibration. Additionally the fluid, generally water, acts to cool the casing, the vibrator, the insert assembly and the tool assembly thereby extending the life of these parts and preventing the hand held instrument from becoming overheated.

Another feature of the device according to the preferred embodiment is the biasing open of the annular nozzle on the same side that work is being done by the tool. That is, as the tool is applied to the work area, a certain amount of force is transferred by the tip of the tool through the tool assembly which acts to open somewhat that side of the nozzle 78 which is on the side of the tool contacting the work area. This of course creates a somewhat larger flow area on that side of the tool where the work area is located. This allows for the greater delivery of cooling fluid to the side of the tool on which work is being done. Advantages inherent in this mode of operation are readily apparent to one skilled in the art.

Another preferred embodiment of the device according to this invention is shown in FIG. 4 of the drawings in cross-sectional elevation of the front half of the device. As shown, an insert assembly 84, like insert assembly 44 is insertably mounted in the housing. As previously mentioned the importance of this feature is in the ready separation and removal or insertion and assembly of the insert assembly within the housing, assuring ease of interchange of the insert assembly and tool tip desired. The insert 84 comprises an outersleeve 85 which is preferably molded out of a structural plastic as two longitudinal halves and permanently bonded upon assembly. The unitary sleeve 86 has a bore 90 therethrough somewhat larger than that provided in the other versions of the device described hereinbefore. This is because of the difficulty to a certain extent of manufacturing the plastic halves to close tolerances.

For interchangability, the sleeve 84 has a rear portion 92 of the same outside diameter as sleeve 44, with an annular groove thereon for placement of an O-ring 96 to assure sealing and securing of the insert in the housing. The middle portion of the sleeve 84 has a relatively larger diameter to provide added strength for internal passages, to abutt against the housing, and to provide sufficient space adjacent the nodal point of the vibrating tool assembly for various cutouts.

Interior of the sleeve on the inside surface of the bore at the nodal point, an annular groove 98 is transversely located, that is, at the point which corresponds to the location of screws 76 on the other embodiment described herein before. The tubular shank 68 located within the bore has a ring 100 brazed onto the shaft adjacent the nodal point and sized to loosely fit into the groove 98. The ring 100 has a single key 102 on its outer circumferance which key fits into one of two semi-circular bypasses 104 located longitudinally on the inner surface of the bore, 180° apart from each other and centered with their radius or altitude on the groove 98. The key is held in one of the bypasses after assembly. The bypasses therefore serve a two part function as a retainer for the key and to provide a path for fluid around the ring.

The front portion of the sleeve has a tranverse groove 106 adjacent its end which groove is adapted to secure a bushing 108 which encircles the shank. The bushing has a flange 110 which fits into the forward groove 106. Functionally the bushing provides an annular nozzle 112 of controlled distance between its inside surface and the outside of the shank regardless of the tolerances of the plastic sleeve. Similarly the bushing most likely prevents wear on the end of the sleeve which would result from the action of the exiting stream of fluid and the vibration of the shank, were it not present. For purposes of inducing an added amount of spray towards the bent side of the tool tip a longitudinal shallow channel 114 is formed on the shank extending for a distance from the interior of the sleeve bore, past the bushing and towards the tool tip. In point of operation both of the versions of the invention described herein operate in a similar manner, the version having the bushing and the plastic sleeve being somewhat cheaper to manufacture and including various improvements and modifications, as for instance the shallow channel for directing extra water towards the area of the tool tip.

Having thus fully described my invention either directly or by reference to prior patents cited herein and wishing to cover those variations and modifications which would be apparent to one skilled in the art, without departing from the spirit and scope thereof,

I claim:

1. In an ultrasonic device having a casing, an energyzing means adjacent said casing, ultrasonic vibration means mounted in said casing and activated by said energyzing means, means for introducing fluid into an end of said casing, the improvement comprising
   a hollow sleeve adapted to be insertably mounted in the end of the casing and in fluid communication therewith,
   connecting means attached to one end of said vibration means and extending through said hollow sleeve, said connecting means being mounted at a spaced distance from the internal walls of said hollow sleeve, forming an annular nozzle adjacent said hollow sleeve anterior end for fluid to exit said nozzle in substantially a 360° annular stream, and tool means axially fixed to said connecting means at the anterior end thereof.

2. The device according to claim 1 wherein said hollow sleeve additionally comprises support means transversely mounted on the inside of said sleeve for supporting said connecting means at the approximate nodal point thereof.

3. The device according to claim 1 wherein said annular space between said hollow sleeve and said connecting means is sufficiently small to induce the fluid flow at the nozzle to exit as a spray.

4. The device according to claim 1 wherein said nozzle
   is biased toward the side of application of force to the tool means.

5. The device according to claim 2 wherein said support means comprises three equally spaced screws threadedly and insertably mounted in three equal spaced threaded holes at 120° apart on said hollow sleeve, the tip of each of said screws being in contact with said connecting means.

6. The device according to claim 5 wherein said annular space between said hollow sleeve and said connecting means is sufficiently small to induce the fluid flow at the nozzle to exit as a spray.

7. The device according to claim 5 wherein said nozzle opening is biased toward the side of application of force to the tool means.

8. The device according to claim 5 wherein said screws are soft tipped.

9. The device according to claim 5 wherein said casing is tubular and said energyzing means is a winding about said casing, said casing and said winding being enclosed within a housing.

10. The device according to claim 1 wherein said nozzle means comprises a bushing mounted internally in said hollow sleeve adjacent the open end thereof, said bushing having an internal diameter at a spaced distance from said connecting means thereby providing an annular nozzle.

11. In an ultrasonic device having a casing, an energyzing means adjacent said casing, means for introducing fluid into an end of said casing and an insert assembly insertably mounted in said casing, the improvement in said insert assembly comprising a hollow sleeve adapted to be insertably mounted in the end of the casing and in fluid connection therewith, connecting means extending through said hollow sleeve, said connecting means comprising a shank being mounted at a spaced distance from the internal walls of said hollow sleeve to thereby form an annular space between said sleeve and said shank said annular space being in fluid communication with said casing, and an annular nozzle adjacent said hollow sleeve anterior end for fluid to exist therefrom, said connecting means also comprising a ring transversely mounted on said shank at the nodal point thereof, said hollow sleeve having an internally located transverse slot adapted to accomodate said ring, and a flow detour means for conducting fluid around said ring and into said annular space ultrasonic vibration means fixedly connected to said connecting means at the posterior end thereof, and adapted to be inserted into said casing into position to be acted upon by said energyzing means, and tool means axially fixed to said connecting means at the anterior end thereof, said tool means being vibrated by the ultrasonic vibration of said vibration means as transmitted by said connecting means.

12. The device according to claim 11 wherein said nozzle additionally comprises a bushing mounted internally in said hollow sleeve adjacent the open end thereof, said bushing having an internal diameter at a spaced distance from said shank forming said annular nozzle.

13. In an ultrasonic device having a casing, an energyzing means adjacent said casing, means for introducing fluid into an end of said casing, and and insert assembly insertably mounted in said casing, the improved insert assembly comprising a hollow sleeve adapted to be insertably mounted in the casing and in fluid communication therewith connecting means extending through said hollow sleeve, said connecting means being mounted at a spaced distance from the internal wall of said hollow sleeve to thereby form an annular space between said sleeve and said connecting means, said annular space being in fluid communication with said casing, and a nozzle means adjacent said hollow sleeve anterior end for fluid flowing through said space to exit said nozzle means said nozzle means comprising a bushing mounted internally in said hollow sleeve adjacent the open anterior end thereof said bushing having an internal diameter at a spaced distance from said connecting means thereby providing an annular nozzle.

said connecting means additionally comprising a shank portion extending through said hollow sleeve, a shallow channel longitudinally located thereon extending from the interior of said hollow sleeve and past said bushing for providing an added stream of fluid, and a ring transversely mounted on said shank portion at the nodal point thereof, said hollow sleeve having a transverse slot adapted to accomodate said ring and flow detour means for providing fluid passages around said ring, ultrasonic vibration means fixedly connected to said connecting means at the posterior end thereof and adapted to be inserted into said casing into position to be acted upon by said energyzing means, and tool means axially fixed to said connecting means at the anterior end thereof, said tool means being vibrated by the ultrasonic vibration of said vibration means as transmitted by said connecting means.

14. A method of utilizing fluid in an ultrasonic device and at a work area around the ultrasonic device tool tip, the method comprising introducing said fluid into the ultrasonic device cooling vibration means within the device by passing said fluid over the vibration means cooling a connecting means attached to the vibration means by forcing the fluid through an annular space between the connecting means and a hollow sleeve, simultaneously with said step of cooling the connecting means, attenuating vibratory transfer from the connecting means to the sleeve, and spraying said fluid in a 360° area about a tool attached to the connecting means.

15. The method of claim 14 wherein an added spray is directed at a point nearest the tool.

* * * * *